(12) United States Patent
Lange et al.

(10) Patent No.: US 9,333,493 B2
(45) Date of Patent: May 10, 2016

(54) REGENERATION OF ALDEHYDE DECARBONYLATION CATALYSTS

(71) Applicant: SHELL OIL COMPANY, Houston, TX (US)

(72) Inventors: Jean-Paul Andre Marie Joseph Gishlain Lange, Amsterdam (NL); Sipke Hidde Wadman, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 14/437,210

(22) PCT Filed: Oct. 22, 2013

(86) PCT No.: PCT/EP2013/072016
§ 371 (c)(1),
(2) Date: Apr. 21, 2015

(87) PCT Pub. No.: WO2014/064070
PCT Pub. Date: May 1, 2014

(65) Prior Publication Data
US 2015/0298103 A1    Oct. 22, 2015

(30) Foreign Application Priority Data
Oct. 23, 2012  (EP) ..................... 12189605

(51) Int. Cl.
*B01J 38/10*    (2006.01)
*B01J 23/96*    (2006.01)
*B01J 37/10*    (2006.01)
*B01J 23/94*    (2006.01)
*C07D 307/36*    (2006.01)
*B01J 23/42*    (2006.01)
*B01J 23/44*    (2006.01)
*B01J 23/58*    (2006.01)

(52) U.S. Cl.
CPC    *B01J 23/96* (2013.01); *B01J 23/42* (2013.01); *B01J 23/44* (2013.01); *B01J 23/58* (2013.01); *B01J 23/94* (2013.01); *B01J 37/10* (2013.01); *B01J 38/10* (2013.01); *C07D 307/36* (2013.01); *Y02P 20/584* (2015.11)

(58) Field of Classification Search
CPC ....................................................... B01J 38/10
USPC ............................................................ 502/53
See application file for complete search history.

(56) References Cited

FOREIGN PATENT DOCUMENTS

| CN | 102256956 | 11/2011 |
|---|---|---|
| RU | 1785731 | 1/1993 |
| WO | 2010071745 | 6/2010 |
| WO | 2010080290 | 7/2010 |
| WO | 2011026061 | 3/2011 |

OTHER PUBLICATIONS

Zhang et al.; "A study of furfural decarbonylation on K-doped Pd/Al2O3"; journal of Molecular Catalysis A: Chemical; vol. 335; pp. 71-81; 2011.

*Primary Examiner* — Edward Johnson

(57) ABSTRACT

The invention relates to a process for regenerating a catalyst used in the decarbonylation of an aldehyde, wherein the catalyst is a heterogeneous, supported catalyst containing a metal selected from the group consisting of Fe, Ru, Os, Co, Rh, Ir, Ni, Pd, Pt and mixtures thereof, and wherein the catalyst is subjected to a gas stream comprising hydrogen at a temperature of from 200 to 600° C., wherein substantially no oxygen is used in the regeneration process.

11 Claims, No Drawings

REGENERATION OF ALDEHYDE DECARBONYLATION CATALYSTS

PRIORITY CLAIM

The present application is the National Stage (§371) of International Application No. PCT/EP2013/072016, filed Oct. 22, 2013, which claims priority from European Patent Application 12189605.4, filed Oct. 23, 2012, incorporated herein by reference.

FIELD OF THE INVENTION

The present invention relates to a process for regenerating a catalyst used in the decarbonylation of an aldehyde.

BACKGROUND OF THE INVENTION

It is known that after a period of time heterogeneous, supported catalysts used in the decarbonylation of aldehydes at an elevated temperature become deactivated, for example by carbonaceous deposit (often called coke) on the catalyst. Such deactivation is shown by a lower conversion, lower selectivity and/or lower yield of the desired decarbonylated compound. An example of such decarbonylation is the decarbonylation of furfural (2-formylfuran) to furan, as shown below. Furan is an important intermediate in the production of tetrahydrofuran (THF) and 1,4-butanediol (BDO).

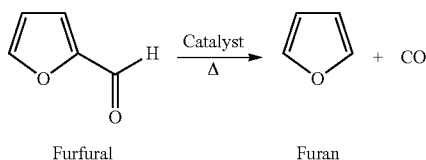

Furfural          Furan

Deactivated decarbonylation catalysts need to be regenerated again. It is known to regenerate by burning off coke from such deactivated catalysts by using a gas stream comprising oxygen, such as an air stream, at an elevated temperature.

For example, WO2010080290 discloses a process for the decarbonylation of specified aldehydes, including furfural, using a Pd/alumina catalyst that has been promoted with an alkali carbonate while heating. Further, WO2010080290 discloses regenerating said catalyst by feeding air, or by feeding a mixture of air and steam or nitrogen, at a temperature of 300-500° C.

In Example 2 of WO2010080290, furfural was decarbonylated using hydrogen and a Pd/alumina catalyst treated with cesium carbonate. The initial reaction temperature was 270° C. After the conversion of furfural dropped, the reaction temperature was raised to 280° C. and then to 290° C. in order to increase the furfural conversion. Such temperature increase during the decarbonylation of furfural, while furfural is still being fed, may initially result in a somewhat higher conversion but in the long term it will disadvantageously result in an increased catalyst deactivation rate. Table 2 of WO2010080290 shows that the final furfural conversion was only 39.2%. Therefore, such treatment does not regenerate the catalyst.

In Example 3 of WO2010080290, an air feed and a vaporized water (steam) feed were used, said water feed containing about 2 vol. % of oxygen, to regenerate the catalyst from Example 2 by burning off the carbon from the catalyst at an elevated temperature (330-350° C.). The reactor was then purged with nitrogen and the air and water feeds were stopped. The regenerated catalyst was then tested again for furfural decarbonylation, by lowering the temperature (to 290° C.) and resuming a hydrogen flow and a furfural flow. In Example 5 of WO2010080290, an air feed and a nitrogen feed were used for regeneration.

Also WO2010071745 discloses regeneration of furfural decarbonlyation catalysts using air.

Oxidative catalyst regeneration using air is a cumbersome treatment that implies multiple operation steps, dedicated equipment to feed the reactor with either pure $N_2$ (for purge) or air (for coke burn-off). Further, this requires an accurate reactor monitoring for avoiding runaway during the coke burn-off. By applying oxidative catalyst regeneration there is also the hazard connected with a possible mixing of $H_2$ that may be used for the decarbonylation reaction and $O_2$ needed for the regeneration. A further drawback of oxidative catalyst regeneration is that this cannot be applied to catalysts which comprise carbon as a support, because the carbon support would also be burnt under such oxidative conditions.

It is an object of the present invention to provide a process for regenerating a heterogeneous, supported catalyst used in the decarbonylation of an aldehyde, which process does not have the above drawbacks.

SUMMARY OF THE INVENTION

Surprisingly it was found that by subjecting a heterogeneous, supported catalyst used in the decarbonylation of an aldehyde to a gas stream comprising hydrogen at a temperature of from 200 to 600° C., the catalyst is regenerated in terms of achieving a higher conversion, higher selectivity and/or higher yield of the desired decarbonylated compound.

Accordingly, the present invention relates to a process for regenerating a catalyst used in the decarbonylation of an aldehyde, wherein the catalyst is a heterogeneous, supported catalyst containing a metal selected from the group consisting of Fe, Ru, Os, Co, Rh, Ir, Ni, Pd, Pt and mixtures thereof, and wherein the catalyst is subjected to a gas stream comprising hydrogen at a temperature of from 200 to 600° C.

It was found that, in contrast with oxidative catalyst regeneration using air, the decarbonylation catalyst can be regenerated in the process of present invention by applying a relatively simple treatment with hydrogen ($H_2$) at an elevated temperature (200 to 600° C.). This allows for a simpler and faster catalyst regeneration containing less process steps, wherein a runaway during coke burn-off cannot take place. Furthermore, because substantially no $O_2$ is used in the present process, there is neither any hazard connected with a possible mixing of $H_2$ that may be used for the decarbonylation reaction and $O_2$ needed for the regeneration. Furthermore, in the present invention, no additional equipment is needed, such as dedicated pipelines with valves, flow meters, mixers and controllers to feed air (or air diluted with $N_2$) for regeneration and to accommodate the effluent. In the present invention, neither any additional gas tanks for $N_2$ and air or air blowers (with purification) are needed. Still further, because substantially no $O_2$ is used in the present regeneration process, the latter process can be applied to catalysts which have (activated) carbon as a support, because the carbon support would not burnt under such non-oxidative conditions.

DETAILED DESCRIPTION OF THE INVENTION

In the present invention, a catalyst is regenerated that was used in the decarbonylation of an aldehyde.

Said aldehyde is preferably a compound of the following formula:

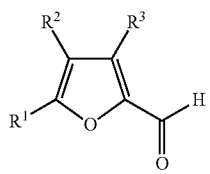

wherein $R^1$, $R^2$ and $R^3$ are each independently selected from hydrogen, a formyl group, a $C_1$ to $C_4$ hydroxyalkyl group and a $C_1$ to $C_4$ hydrocarbyl group. A formyl group has the formula —(C=O)H. Further, said $C_1$ to $C_4$ hydroxyalkyl group is an alkyl group having from 1 to 4 carbon atoms, for example a linear alkyl group having from 1 to 3 carbon atoms, wherein one or more of the hydrogen atoms is replaced by one or more hydroxy groups. Preferably, said $C_1$ to $C_4$ hydroxyalkyl group is a hydroxymethyl group (—$CH_2OH$). Still further, said $C_1$ to $C_4$ hydrocarbyl group may be an alkyl group having from 1 to 4 carbon atoms, for example a linear alkyl group having from 1 to 3 carbon atoms. Preferably, said alkyl group is a methyl group.

Preferably, said aldehyde is a compound of the above formula wherein $R^1$, $R^2$ or $R^3$, preferably $R^1$, is a formyl group, a hydroxymethyl group or a methyl group and the remaining two substituents selected from $R^1$, $R^2$ and $R^3$ are hydrogen, or wherein all of $R^1$, $R^2$ and $R^3$ are hydrogen, preferably wherein all of $R^1$, $R^2$ and $R^3$ are hydrogen. More preferably, the aldehyde is 2,5-diformylfuran, 2-formyl-5-hydroxymethylfuran, 2-formyl-5-methylfuran, 2-formylfuran or a mixture thereof, preferably 2-formylfuran. 2-Formylfuran is furfural and is a compound of the above formula wherein all of $R^1$, $R^2$ and $R^3$ are hydrogen.

The catalyst to be regenerated in the present invention may be a deactivated catalyst. By "deactivated catalyst" a catalyst is meant of which the activity is reduced over time as compared to its original activity (under the same conditions). Said activity is measured by measuring the conversion of the starting material after contacting with the catalyst under the same conditions (such as temperature). Preferably, said activity for the deactivated catalyst is reduced by at most 99.9%, more preferably at most 99%, more preferably at most 90%, more preferably at most 80%, more preferably at most 70%, more preferably at most 60%, more preferably at most 50%, more preferably at most 40%, more preferably at most 30%, more preferably at most 20%, more preferably at most 10% and most preferably at most 5% as compared to the original activity of said catalyst (under the same conditions).

Preferably, in the present invention, the catalyst is regenerated in the absence of the aldehyde. This may be achieved by shutting off the aldehyde feed stream to the reactor and, optionally, purging the reactor for a period of time before the catalyst regeneration is started.

In the present invention, the catalyst is regenerated by subjecting it to a gas stream comprising hydrogen at a temperature of from 200 to 600° C., for example 250 to 450° C., preferably in the absence of the aldehyde as discussed above. Further, preferably, said regeneration temperature is higher than the reaction temperature. Said reaction temperature is the temperature at which the aldehyde was decarbonylated before the catalyst regeneration process of the present invention is started. More preferably, said regeneration temperature is higher than the initial reaction temperature, which is the reaction temperature at the beginning of the preceding decarbonylation reaction. The latter initial reaction temperature is the lowest reaction temperature in a case wherein the reaction temperature is increased over time during the preceding decarbonylation reaction. Said reaction temperature is not essential and may be of from 100 to 450° C., preferably of from 100 to 350° C., more preferably of from 200 to 350° C., most preferably of from 200 to 300° C. Preferably, said regeneration temperature is at least 10° C. higher, more preferably at least 25° C. higher, more preferably at least 75° C. higher, more preferably at least 100° C. higher and most preferably at least 125° C. higher than the reaction temperature, suitably the initial reaction temperature. Further, preferably, said regeneration temperature is at most 350° C. higher, more preferably at most 300° C. higher, more preferably at most 250° C. higher, more preferably at most 200° C. higher, more preferably at most 150° C. higher and most preferably at most 100° C. higher than the reaction temperature, suitably the initial reaction temperature.

The gas stream that is used in the catalyst regeneration process of the present invention and which comprises hydrogen, may comprise one or more additional gases. Said additional gas(es) may be selected from the group consisting of the noble gases, nitrogen ($N_2$), carbon monoxide (CO) and steam. Preferably, if an additional gas is used, it is $N_2$. A suitable noble gas is argon. Preferably, if one or more additional gases are used, said gas stream comprises hydrogen and the additional gas(es), for example $N_2$, in a volume ratio which is greater than 0.01:1 ($H_2$:additional gas or gases), more preferably greater than 0.1:1, more preferably greater than 1:1, more preferably greater than 5:1, more preferably greater than 10:1, more preferably greater than 50:1, more preferably greater than 100:1 and even more preferably greater than 1000:1. Most preferably, the gas stream used in the catalyst regeneration process of the present invention consists of hydrogen, which means that it contains substantially no gases other than the hydrogen gas. For example, in the latter embodiment, the amount of hydrogen in said gas stream may be greater than 99 vol. %, suitably greater than 99.9 vol. %, more suitably greater than 99.99 vol. %.

Preferably, the flow of $H_2$ (per gram of catalyst and per hour) used during the catalyst regeneration process of the present invention is greater than the flow of $H_2$ (per gram of catalyst and per hour), if any, used during the preceding aldehyde decarbonylation process.

In a further embodiment, the gas stream to be used in the catalyst regeneration process of the present invention may be the gas stream leaving the preceding aldehyde decarbonyation process in a case wherein during the latter process hydrogen gas ($H_2$) was present. Thus, the latter (outlet) gas stream comprises at least said $H_2$, carbon monoxide (CO) and furan product. The furan product would be inert. In this way, said $H_2$ is re-used, thereby lowering capital expenditure, without furan product being lost. This embodiment is particularly advantageous in a case wherein several reactors are operated in swing operation. A reactor under regeneration mode may then be fed by the gas effluent of one or more reactors under decarbonylation mode.

Substantially no oxygen is used in the regeneration process. Unlike in prior art processes, the catalyst is not heated in the presence of oxygen before treatment with the gas stream comprising hydrogen.

Preferably, in view of the presence of $H_2$, no $O_2$ is present in the gas stream comprising hydrogen used in the catalyst regeneration process of the present invention. If, however, some $O_2$ is present in said gas stream, the amount thereof is suitably smaller than 1 vol. %, suitably smaller than 0.01 vol. %, more suitably smaller than 0.001 vol. %, most suitably smaller than 0.0001 vol. %.

The pressure of the gas stream comprising hydrogen used in the catalyst regeneration process of the present invention may be in the range of from 1 to 100 bar, suitably 2 to 30 bar, more suitably 3 to 15 bar. Further, the hydrogen gas may be fed at a rate of 0.01 to 100 Nl/g/h (normal liter per gram of catalyst per hour), preferably 0.1 to 50 Nl/g/h, more preferably 1 to 10 Nl/g/h.

In the present invention, the decarbonylation catalyst is a heterogeneous, supported catalyst. Further, said catalyst should contain a metal selected from the group consisting of iron (Fe), ruthenium (Ru), osmium (Os), cobalt (Co), rhodium (Rh), iridium (Ir), nickel (Ni), palladium (Pd), platinum (Pt) and mixtures thereof.

Preferably, said metal from the catalyst is selected from the group consisting of Rh, Ir, Pd, Pt and mixtures thereof. More preferably, said metal from the catalyst is selected from the group consisting of Pd, Pt and a mixture of Pd and Pt. Even more preferably, said metal from the catalyst is Pd or Pt. Most preferably, said metal from the catalyst is Pd.

The total amount of the metal(s) selected from the group consisting of Fe, Ru, Os, Co, Rh, Ir, Ni, Pd, Pt and mixtures thereof may vary within wide ranges, and may be of from 0.01 to 20 wt. %, 0.1 to 10 wt. % or 0.5 to 5 wt. % on the basis of the total weight of the catalyst. Preferably, the total amount of said metal(s) is at least 0.01 wt. %, more preferably at least 0.05 wt. %, more preferably at least 0.1 wt. %, more preferably at least 0.3 wt. %, more preferably at least 0.5 wt. %, most preferably at least 0.7 wt. %. Further, preferably, the total amount of said metal(s) is at most 20 wt. %, more preferably at most 15 wt. %, more preferably at most 10 wt. %, more preferably at most 8 wt. %, more preferably at most 5 wt. %, most preferably at most 3 wt. %.

Further to the above-mentioned metal(s), the catalyst used in the present invention may contain one or more additional metals, for example promotor metals. Suitable examples of such additional metals are alkali metals and/or alkaline earth metals. Preferably, the alkali metal is selected from the group consisting of sodium, potassium, rubidium and cesium. More preferably, the alkali metal is potassium.

The total amount of said additional metal(s) may vary within wide ranges, and may be of from 0.1 to 25 wt. %, 0.5 to 15 wt. % or 1 to 10 wt. % on the basis of the total weight of the catalyst.

The nature of the support for the catalyst used in the present invention is not essential. Said support may comprise carbon or one or more oxides selected from the group consisting of silica, alumina, barium sulfate, titanium dioxide, zirconium dioxide, magnesium silicate, diatomaceous earth and silica gel. Preferably, the support comprises carbon, silica, alumina or a mixture thereof. In case the support comprises carbon, it may comprise for example activated carbon or carbon fibres.

During the aldehyde decarbonylation that precedes the catalyst regeneration process of the present invention, the aldehyde may be contacted with the catalyst, as defined above, at a temperature of from 100 to 450° C., preferably of from 100 to 350° C., more preferably of from 200 to 350° C., most preferably of from 200 to 300° C., as mentioned above. The pressure during the aldehyde decarbonylation may be in the range of from 1 to 100 bar, suitably 2 to 30 bar, more suitably 3 to 15 bar. The aldehyde is the aldehyde as defined above. Said aldehyde decarbonylation may be carried out in liquid phase or gas phase, which means that the aldehyde is either liquid or gaseous. Preferably, it is carried out in gas phase. Furthermore, during the aldehyde decarbonylation, $H_2$ may be present or absent. If $H_2$ is present, the molar ratio of $H_2$:aldehyde may be greater than 0.1:1, greater than 1:1, greater than 10:1, or greater than 100:1. Further, if $H_2$ is present, the gas stream that is used in the aldehyde decarbonylation and which comprises hydrogen, may comprise one or more additional gases. Said additional gas(es) may be selected from the group consisting of the noble gases, nitrogen ($N_2$), carbon monoxide (CO) and steam. Preferably, if an additional gas is used, it is $N_2$. A suitable noble gas is argon. Preferably, if one or more additional gases are used, said gas stream comprises hydrogen and the additional gas(es), for example $N_2$, in a volume ratio which is greater than 0.01:1 ($H_2$:additional gas or gases), more preferably greater than 0.1:1, more preferably greater than 1:1, more preferably greater than 5:1, more preferably greater than 10:1, more preferably greater than 50:1, more preferably greater than 100:1 and even more preferably greater than 1000:1. Further, if $H_2$ is present during the aldehyde decarbonylation, the hydrogen gas may be fed at a rate of 0.01 to 100 Nl/g/h (normal liter per gram of catalyst per hour), preferably 0.1 to 50 Nl/g/h, more preferably 1 to 10 Nl/g/h. Further, the aldehyde (e.g. furfural) may be fed at a rate of from 0.1 to 100 g/g/h (gram per gram of catalyst per hour), suitably 0.5 to 10 g/g/h.

The catalyst regeneration process of the present invention is illustrated by the following Examples.

EXAMPLES

Each of the experiments was carried out in a steel reactor having an internal diameter of 4.6 mm and a length of 35 cm. A charge of 0.5 g of crushed catalyst particles, having sizes ranging from 0.2 to 0.6 mm, was placed in the middle of the reactor between two inert beds of SiC (silicon carbide).

At the beginning of the experiment, the catalyst was reduced by subjecting it to a temperature of 400° C. and to 10 bar of a gas stream comprising nitrogen and hydrogen in a volume ratio of 10:1 ($N_2$:$H_2$). Said gas stream was fed at 6.25 Nl/g/h (normal liter per gram of catalyst per hour) for 18 hours. Subsequently, the catalyst was cooled to 250° C. and furfural was then fed at a rate of 0.75 g/g/h (gram per gram of catalyst per hour) while maintaining said gas stream comprising nitrogen and hydrogen. Prior to contacting the catalyst, the liquid furfural was vaporized at the top of the reactor bed. The gaseous reaction product stream leaving the reactor was further diluted with nitrogen gas and maintained at a temperature of 150° C. Said reaction product was analyzed by on-line gas chromatography (GC). The furfural feed contained 3 wt. % of cyclopentane that was used as internal standard for GC analysis.

Thus, during the decarbonylation reaction step, 0.75 g of furfural was contacted with 6.25 Nl of a gas stream comprising $N_2$:$H_2$ in a volume ratio of 10:1. This corresponds with a molar ratio of $H_2$:furfural, during the decarbonylation reaction step, of 3.3:1.

The catalyst was used for a certain period of time after which the catalyst was regenerated. The regeneration was performed as follows:

a. the furfural feed stream was shut off;
b. said gas stream comprising nitrogen and hydrogen was replaced by a gas stream only consisting of hydrogen which was fed at 6.25 Nl/g/h (10 bar);
c. the reactor was purged using the latter gas stream for 2 hours;
d. the reactor temperature was raised from 250° C. to an elevated temperature, as further described below, at a rate of 1° C./min;

e. said regeneration conditions were maintained for 18 hours;
f. the reactor was cooled to 250° C. at a rate of 1° C./min;
g. said gas stream only consisting of hydrogen was replaced by a gas stream comprising nitrogen and hydrogen in a volume ratio of 10:1 ($N_2$:$H_2$) which was fed at 6.25 Nl/g/h (10 bar);
h. the reactor was purged using the latter gas stream for 1 hour;
i. the furfural feed stream was resumed.

A first catalyst regeneration was performed after 25 hours on stream, at an elevated temperature of 400° C., while a second catalyst regeneration was performed after 50 hours on stream, at an elevated temperature of 300° C. By said "hours on stream" reference is made to the furfural feed stream. That is, the time period needed for carrying out the regeneration procedure, during which the furfural feed stream was shut off, is not taken into account.

Four experiments, each using a different catalyst, were performed. In the table below, these catalysts are identified. These catalysts were prepared by incipient wetness impregnation of a support (silica or alumina) with a salt of a noble metal (Pd or Pt) and optionally with a potassium salt thereafter (only for the catalyst used in Experiment 3). The catalysts were subsequently calcined in air at 450° C. for 4 hours.

Further, in the table below, the conversion, selectivity and yield are mentioned, both before and after the second catalyst regeneration (at 50 hours on stream).

| Experiment; catalyst[5] | TOS[1] | Conversion[2] | Selectivity[3] | Yield[4] |
|---|---|---|---|---|
| Experiment 1 | 31 | 57 | 59 | 34 |
| 1% Pd/$SiO_2$ | 48 | 53 | 54 | 29 |
|  | 52 | 62 | 60 | 37 |
| Experiment 2 | 43 | 44 | 50 | 22 |
| 1% Pd/$Al_2O_3$ | 46 | 39 | 45 | 18 |
|  | 51 | 70 | 57 | 40 |
| Experiment 3 | 27 | 92 | 74 | 68 |
| 1% Pd/5% K/$Al_2O_3$ | 44 | 79 | 77 | 61 |
|  | 52 | 98 | 97 | 95 |
| Experiment 4 | 28 | 90 | 78 | 70 |
| 1% Pt/$Al_2O_3$ | 41 | 70 | 83 | 59 |
|  | 66 | 99 | 66 | 66 |

[1]TOS = time on (furfural feed) stream (in hours)
[2]Conversion of furfural (in mole %)
[3]Selectivity to furan (in mole %)
[4]Yield of furan (in mole %)
[5]Percentages are weight percentages and are based on the total weight of the catalyst.

From the table above it can be seen that in all of the experiments the conversion of furfural and the yield of furan were increased by the catalyst regeneration (at 50 hours on stream). Further, in experiments 1 to 3, also the selectivity to furan was increased by said catalyst regeneration. In experiment 4, no product analysis was performed directly after the regeneration, only after 66 hours on stream.

That which is claimed is:

1. A process for regenerating a catalyst used in the decarbonylation of an aldehyde, wherein the catalyst is a heterogeneous, supported catalyst containing a metal selected from the group consisting of Fe, Ru, Os, Co, Rh, Ir, Ni, Pd, Pt and mixtures thereof, and wherein the catalyst is subjected to a gas stream comprising hydrogen at a temperature of from 200 to 600° C., wherein substantially no oxygen is used in the regeneration process, and wherein the catalyst is not heated in the presence of oxygen before treatment with the gas comprising hydrogen.

2. A process according to claim 1, wherein the aldehyde is a compound of the following formula:

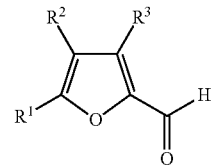

wherein R1, R2 and R3 are each independently selected from hydrogen, a formyl group, a C1 to C4 hydroxyalkyl group and a C1 to C4 hydrocarbyl group.

3. A process according to claim 2, wherein R1, R2 or R3, preferably R1, is a formyl group, a hydroxymethyl group or a methyl group and the remaining two substituents selected from R1, R2 and R3 are hydrogen, or wherein all of R1, R2 and R3 are hydrogen, preferably wherein all of R1, R2 and R3 are hydrogen.

4. A process according to claim 3, wherein the aldehyde is 2,5-diformylfuran, 2-formyl-5-hydroxymethylfuran, 2-formyl-5-methylfuran, 2-formylfuran or a mixture thereof, preferably 2-formylfuran.

5. A process according to claim 1, wherein the catalyst is regenerated in the absence of the aldehyde.

6. A process according to claim 1, wherein the catalyst is regenerated at a temperature which is higher than the reaction temperature, preferably at a temperature which is at least 10° C. higher and at most 250° C. higher than the reaction temperature.

7. A process according to claim 1, wherein the gas stream comprising hydrogen comprises one or more additional gases in a volume ratio of hydrogen to additional gas or gases which is greater than 0.01:1.

8. A process according to claim 1, wherein the gas stream comprising hydrogen consists of hydrogen.

9. A process according to claim 1, wherein the metal is selected from the group consisting of Rh, Ir, Pd, Pt and mixtures thereof, preferably from the group consisting of Pd, Pt and a mixture of Pd and Pt.

10. A process according to claim 1, wherein the catalyst contains one or more additional metals selected from alkali metals and alkaline earth metals.

11. A process according to claim 1, wherein the support for the catalyst comprises carbon, silica or alumina.

* * * * *